(12) United States Patent
Serban et al.

(10) Patent No.: US 10,254,217 B2
(45) Date of Patent: Apr. 9, 2019

(54) BENZENE SENSORS AND ASSOCIATED METHODS

(71) Applicant: Honeywell International Inc., Morris Plains, NJ (US)

(72) Inventors: Bogdan Serban, Bucharest (RO); Octavian Buiu, Bucharest (RO); Mihai Brezeanu, Bucharest (RO); Cornel Cobianu, Bucharest (RO); Cazimir Gabriel Bostan, Bucharest (RO); Cristian Diaconu, Bucharest (RO)

(73) Assignee: Honeywell International, Inc., Morris Plains, NJ (US)

( * ) Notice: Subject to any disclaimer, the term of this patent is extended or adjusted under 35 U.S.C. 154(b) by 142 days.

(21) Appl. No.: 15/527,278

(22) PCT Filed: Nov. 11, 2015

(86) PCT No.: PCT/US2015/060160
§ 371 (c)(1),
(2) Date: May 16, 2017

(87) PCT Pub. No.: WO2016/081241
PCT Pub. Date: May 26, 2016

(65) Prior Publication Data
US 2017/0363539 A1  Dec. 21, 2017

Related U.S. Application Data

(60) Provisional application No. 62/081,657, filed on Nov. 19, 2014.

(51) Int. Cl.
*G01N 21/33*  (2006.01)
*G01N 21/76*  (2006.01)
(Continued)

(52) U.S. Cl.
CPC ............. *G01N 21/33* (2013.01); *G01N 21/75* (2013.01); *G01N 27/127* (2013.01); *G01N 31/22* (2013.01);
(Continued)

(58) Field of Classification Search
CPC ... G01N 2021/7756; G01N 2021/7773; G01N 21/33; G01N 21/75; G01N 27/127; G01N 31/22; G01N 33/54366; G01N 33/0047
See application file for complete search history.

(56) References Cited

U.S. PATENT DOCUMENTS 8,367,421 B2 *  2/2013  Schulten ................ G01N 31/22
436/140

FOREIGN PATENT DOCUMENTS

RU  2469295 C1  12/2012
WO  2016/081241 A1  5/2016

OTHER PUBLICATIONS

Ming-Tsun Ke et al.: "A MEMS-based Benzene Gas Sensor with a Self-heating WO3 Sensing Layer", Sensors vol. 9, No. 4, Apr. 21, 2009, pp. 2895-2906. (Year: 2009).*

(Continued)

*Primary Examiner* — Jennifer Wecker
(74) *Attorney, Agent, or Firm* — Wick Phillips Gould & Martin, LLP

(57) ABSTRACT

In an embodiment, a benzene sensor comprises a substrate having an iodine complex disposed thereon, a radiation source configured to project UV radiation onto the complex, and a UV detector configured to detect a UV reflection off of the substrate having the iodine complex. The iodine complex can include a cyclodextrine-iodine complex such as an alpha-cyclodextrine-iodine complex, a β-cyclodextrine iodine complex, or any combination thereof.

20 Claims, 1 Drawing Sheet

(51) Int. Cl.
G01N 21/77 (2006.01)
G01N 31/22 (2006.01)
G01N 27/12 (2006.01)
G01N 33/00 (2006.01)
G01N 21/75 (2006.01)
G01N 21/78 (2006.01)
G01N 33/543 (2006.01)

(52) U.S. Cl.
CPC ... *G01N 33/0047* (2013.01); *G01N 33/54366* (2013.01); *G01N 2021/7756* (2013.01); *G01N 2021/7773* (2013.01)

(56) References Cited

OTHER PUBLICATIONS

International Application No. PCT/US2015/060160, International Search Report dated Mar. 21, 2016, 4 pages.
International Application No. PCT/US2015/060160, Written Opinion of the International Searching Authority dated Mar. 21, 2016, 7 pages.
Nakamoto et al.: "Colorimetric method for odor discrimination using dye-coated plate plate and MultiLED Sensor", Sensors and Actuators B: Chemical, vol. 116, May 2, 2006 pp. 202-206.
H. A. Benesi et al: "Spectophotometry of Iodine With Aromatic Hydrocarbon: A Spectrophotometric Investigation of the Interaction of Iodine with Aromatic Hydrocarbons", Aug. 1, 1949, pp. 2703-2707, retrieved from the internet on May 15, 2017, retrieved from the internet: URL: http://alevine.chem.ucla.edu/Chem114/S 3 Sup. pdf.
Girschikofsky M. et al.: "Optical planar Bragg grating sensor for real-time detection of benzene, toluene and xylene in solvent vapour", Sensors and Actuators B: Chemical, vol. 171-172, Apr. 27, 2012, pp. 338-342.
Ming-Tsun Ke et al.: "A MEMS-based Benzene Gas Sensor with a Self-heating WO3 Sensing Layer", Sensors vol. 9, No. 4, Apr. 21, 2009, pp. 2895-2906.
International Application No. PCT/US2015/060160, International Preliminary Report on Patentability dated May 23, 2017, 8 pages.

* cited by examiner

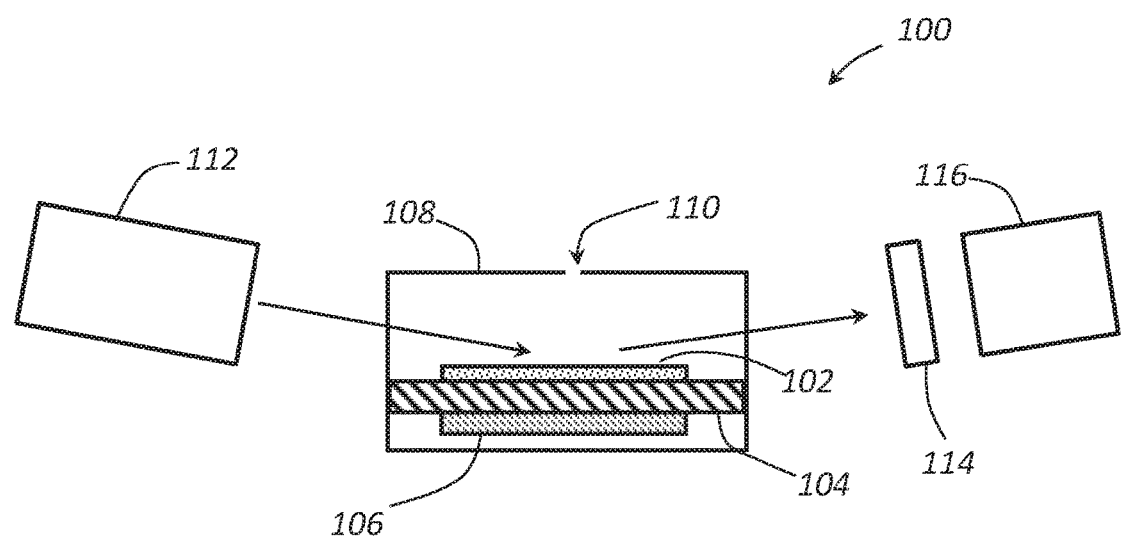

BENZENE SENSORS AND ASSOCIATED METHODS

CROSS-REFERENCE TO RELATED APPLICATIONS

This application is the national stage application of and claims priority to International Application Serial No. PCT/US2015/060160 (entitled BENZENE SENSORS AND ASSOCIATED METHODS filed Nov. 11, 2015), which claims priority to U.S. Provisional Patent Application Ser. No. 62/081,657 (entitled GAS-PHASE BENZENE SENSOR AND ASSOCIATED METHODS filed Nov. 19, 2014), both of which are incorporated herein by reference in their entirety.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Detection of benzene and similar volatile organic compounds (VOC) is of high importance for safety and process control in chemical, petrochemical, steel and other manufacturing industries, as well as for minimizing environment pollution with these harmful gases. Benzene ($C_6H_6$) is a highly flammable, toxic, human carcinogen, organic hydrocarbon. It is widely used as an intermediate in processes leading to plastics, nylon, lubricants, coke, fertilizers, detergents, etc. In recent years, in many regions, including US and EU, benzene has replaced lead in gasoline composition. Due to its increased harmful potential, severe regulations have been imposed against its industrial use. In EU, gas can contain maximum 1% benzene by volume, while in US the upper limit is 0.62%. Monitoring benzene concentration is a vital requirement for the personal protection of people working in oil and gas storage and transportation, oil refineries, petrochemical industry. At concentration levels higher than 10,000 ppm, benzene can be lethal, while repeated exposures at much lower levels can lead to cancer, heart and brain failures, and endocrine diseases. The level over which benzene becomes harmful is currently set at the threshold limit value (TLV) of 0.5 ppm.

Currently, benzene sensing is performed by employing several techniques: multi-gas monitors, metal-oxides (MOx) based chemo-resistors, electrochemical detectors, fixed or portable gas chromatographs, single gas (colorimetric) detection tubes, and/or photoionization detectors (PIDs). A combination of the last two technologies leads to Ultra RAE3000, a portable benzene and compound-specific VOC monitor commercialized by Honeywell's RAE Systems. Ultra RAE3000 employs a PID, a low energy UV lamp and pre-filter tubes. Honeywell top-solution has an accuracy of +/−10%.

Other sensors that are commercially available for such industrial applications, as well as breath alcohol portable detectors, include a thick film of $SnO_2$ deposited on ceramic substrate, which is heated on the other side by a platinum heater. Even if this sensor is recommended not only for domestic applications, but also for portable applications, it is consuming about 660 mW for heating the substrate to the optimum sensing temperature and reading the detector response. Such a level of power consumption is determining a frequent battery replacement in portable applications, which may raise safety issues in the field operation.

In addition, the above noted sensors are detecting these VOC's gases only at relatively high concentrations, above 50 ppm, while the present requirements for benzene in the ambient are as follow: the threshold limit value (TLV) is 0.5 ppm, the short term exposure limit (STEL) is 2.5 ppm, while the immediately dangerous to health and life (IDHL) level is 500 ppm. Therefore, in safety applications, it is useful to detect much lower gas concentrations and then give an alarm and take an early stage action against any hazardous situation. Therefore, there is a strong motivation for increasing the sensitivity of the existing commercial sensors, as well as decreasing power consumption of VOC sensors so that an electric power much below 100 mW to be used and concentrations much below 50 ppm to be detected for VOC gases.

It is already largely accepted by the business and scientific community that the use of nanostructured sensing materials is increasing the sensitivity due to its material architecture and it is allowing the reduction of the power consumption, due to their large specific area and increased porosity, which are thus increasing the number of active sensing sites, while their surface energy is high enough for the sensing reactions to take place without too much thermal energy added from outside.

SUMMARY

In an embodiment, a benzene sensor comprises a substrate having an iodine complex disposed thereon, a radiation source configured to project UV radiation onto the complex, and a UV detector configured to detect a UV reflection off of the substrate having the iodine complex. The iodine complex can include a cyclodextrine-iodine complex such as an alpha-cyclodextrine-iodine complex, a β-cyclodextrine iodine complex, or any combination thereof.

In an embodiment, a method for sensing benzene comprises exposing benzene to an iodine complex, forming an iodine-benzene complex, irradiating the iodine-benzene complex with UV radiation, detecting a UV absorption in the intensity of radiation reflected from the iodine-benzene complex, and determining that benzene is present based on the absorption of the UV radiation in the reflected radiation.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 1 schematically illustrates a benzene sensor according to an embodiment.

DETAILED DESCRIPTION

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Disclosed herein is a VOC sensor that can detect benzene. The sensor includes a chemo-optical sensor using iodine as an absorbent compound. The chemo-optical sensor can include a complex comprising iodine to retain the iodine at the surface of the reflective element. When benzene is present, an iodine-benzene complex can form on the surface that leads to an absorption of specific bands of UV radiation. By detecting the UV radiation reflecting from the surface, the presence of benzene can then be detected.

FIG. 1 schematically illustrates a cross section of a chemo-optical sensor 100 having an iodine complex 102. The sensor 100 can comprise a housing 108 having an aperture 110 or other diffusion barrier disposed therein. A chamber can be formed within the housing 108. A portion of the housing can comprise a substrate 104 carrying a complex 102 on a surface thereof. A heater 106 can be thermally coupled to the substrate 104 and serve to heat the substrate 104 and the complex 102 to a desired operating temperature. A light source 112 can be positioned to provide radiation into the chamber and reflect the radiation off of the complex 102. The reflected radiation can then pass through an optional diffraction grating 114 and pass to a radiation detector 116. In some embodiment, a wave guide such as a fiber optic filament can be positioned to guide the light from the light source 112 to the complex 102 and/or guide the reflected light from the complex 102 to the detector 116.

The sensor 100 may rely on the presence of the complex 102 to react with benzene and form a complex that has a different UV absorbance than the complex 102 outside the presence of benzene. This complex 102 is based on the supramolecular chemistry principles. The low-cost, easy-to-manufacture solution has the potential to go beyond the state-of-the-art in terms of specificity, being able to discriminate between several flammable aromatic hydrocarbons.

The complex 102 can comprise iodine or a complex thereof that can react with benzene. In general, benzene can react with iodine and generate a charge complex which can be easily identified due to its specific UV absorption band. This absorption band is attributed to a partial intermolecular charge transfer between an electron-acceptor (iodine) and an electron-donor (benzene):

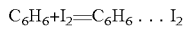

The formation of this type of charge complex can be understood in the terms of the Hard Soft Acid Base (HSAB) rule. According to the HSAB theory, hard acids prefer to react with hard bases, while soft acids prefer to interact with soft base. Since benzene is classified as soft a base and iodine is soft acid, it is expected that these compounds can yield a strong interaction. However, the use of iodine as a sensing material has a drawback. Although a solid, iodine is highly volatile and can sublimate even at room temperature, much less at elevated operating temperatures. In order to stabilize the iodine, the iodine can be encapsulated in a cavity of either α-, β-cyclodextrines (CDs), their derivatives, or combinations thereof. In an embodiment, the iodine complex can comprise a 2-hydroxypropilated-β-cyclodextrines iodine complex, a gamma-cyclodextrine iodine complex, a randomly methylated alpha-cyclodextrine-iodine complex, a randomly methylated beta-cyclodextrine-iodine complex, or any combination thereof. Cyclodextrines are enzyme modified starch derivatives, comprising D-glucose units. Formation constants of cyclodextrine inclusion complexes with iodine were determined by measuring solubility of iodine vapor in water, at about 25° C. (e.g., about $8.3 \times 10^3$ $dm^3\ mol^{-1}$ for α-CD and about $1 \times 10^2\ dm^3\ mol^{-1}$ for β-CD).

The supramolecular cyclodextrine-iodine complex is stable due to the van der Waals forces which exist between the hydrophobic interior of the cyclodextrine as host molecule and iodine as guest molecule. The dissociation of the iodine-cyclodextrine complex can be achieved above room temperature (>50° C.). At the same time, benzene has a significantly larger affinity for iodine than for cyclodextrine. Therefore, when exposed to benzene, the supramolecular cyclodextrine-iodine assembly is expected to liberate iodine, thus leading to a benzene-iodine reaction which can be optically detected.

The complex 102 can comprise the cyclodextrine-iodine complex by itself, or the cyclodextrine-iodine complex disposed on or incorporated into a carrier. In an embodiment, the cyclodextrine-iodine complex can be deposited on a substrate 104 such a polymer (e.g., kapton, polyamide, or the like). The heater 106 can be disposed in thermal contact with the substrate 104. The heat from the heater 106 can heat both the substrate 104 and the complex 102 disposed on the substrate 104 during operation.

The radiation source 112 serves to provide radiation in the ultraviolet spectrum to the complex 102 on the substrate 104. Any suitable source of UV radiation can be used for the radiation source 112, and the radiation source 112 may comprise focusing elements (e.g., lenses, etc.) in addition to radiation emitting elements. In an embodiment, the radiation source can comprise one or more UV lamps (e.g., a deuterium lamp, etc.), light emitting diodes (LEDs), and the like. An integrated power supply can be coupled to the radiation source 112. For example, a 50 to 500 kHz power supply can be used to power the radiation source 112 to initiate and maintain the discharge of the UV radiation.

The radiation provided by the radiation source 112 can be provided within the chamber and one or more windows can be used to allow the radiation to pass into the chamber and reflect off of the complex 102. An optional grating 114 or other kind of spectral filter can be used to filter the UV light and allow a desired portion of the UV spectrum to pass through to the sensor 116. The grating 114 can comprise any material or design configured to allow the desired absorption spectrum to pass through to the sensor 116. Depending on the range of UV radiation emitted by the radiation source 112, the grating 114 or spectral filter may not be needed. The sensor 116 can comprise any sensor sensitive to UV radiation in the absorption band of the complex 102. The radiation detector 116 can comprise a UV GaN, AlGaN, InGaN photodetectors or the like.

An optical detection method based on UV-VIS spectroscopy can be employed to detect the formation of the complex. A beam of non-polarized radiation from the radiation source 112 can be emitted and/or focused on a region of the complex 102 in the chamber. The radiation can be reflected off of the complex 102, pass through the optional grating 114, if present, and be received by the UV detector 116. When benzene is not present, an iodine-benzene complex may not be present on the complex 102, and an intensity of the UV radiation may be at a first level.

When benzene is present in the atmosphere, the benzene may pass into the chamber through the aperture 110 and contact the complex 102. The benzene can react with the active sensing complex (i.e., cyclodextrine & iodine). The benzene exposure can trigger the formation of the iodine-benzene complex, which, in turn, results in a change in the spectral reflection coefficient. As the radiation contacts the iodine-benzene complex, a portion of the UV radiation can be absorbed. The resulting UV radiation reaching the detector 116 may have a decreased intensity as compared to the radiation reaching the detector 116 when benzene is not present. The measured values from the detector 116 can then be compared to reference data (i.e., reflection coefficient for the cyclodextrine-iodine complex prior to benzene exposure) to provide a measure of the amount of benzene present in the atmosphere.

Having described numerous devices, systems, and method herein, various embodiments can include, but are not limited to:

In a first embodiment, a benzene sensor comprises: a substrate having an iodine complex disposed thereon, a radiation source configured to project UV radiation onto the complex; and a UV detector configured to detect a UV reflection off of the substrate having the iodine complex.

A second embodiment can include the benzene sensor of the first embodiment, further comprising: a housing comprising an aperture, wherein the substrate is contained within the housing, and wherein the aperture is the only opening into the housing and the substrate.

A third embodiment can include the benzene sensor of the first or second embodiment, further comprising: a heater in thermal contact with the substrate.

A fourth embodiment can include the benzene sensor of any of the first to third embodiments, wherein the iodine complex comprises an alpha-cyclodextrine-iodine complex.

A fifth embodiment can include the benzene sensor of any of the first to third embodiments, wherein the iodine complex comprises a β-cyclodextrine iodine complex.

A sixth embodiment can include the benzene sensor of any of the first to third embodiments, wherein the iodine complex comprises both an alpha-cyclodextrine-iodine complex and a β-cyclodextrine iodine complex.

A seventh embodiment can include the benzene sensor of any of the first to sixth embodiments, wherein the iodine complex comprises a 2-hydroxypropilated-β-cyclodextrines iodine complex, a gamma-cyclodextrine iodine complex, a randomly methylated alpha-cyclodextrine-iodine complex, a randomly methylated beta-cyclodextrine-iodine complex, or any combination thereof.

In an eighth embodiment, a method for sensing benzene comprises exposing benzene to an iodine complex; forming an iodine-benzene complex; irradiating the iodine-benzene complex with UV radiation; detecting a UV absorption in the intensity of radiation reflected from the iodine-benzene complex; and determining that benzene is present based on the absorption of the UV radiation in the reflected radiation.

A ninth embodiment can include the method of the eighth embodiment, further comprising: heating the iodine complex during the exposure of the benzene to the iodine complex.

A tenth embodiment can include the benzene sensor of the eighth or ninth embodiment, wherein the iodine complex comprises s cyclodextrine-iodine complex.

An eleventh embodiment can include the benzene sensor of any of the eighth to tenth embodiments, wherein forming the iodine-benzene complex comprises; dissociating the iodine complex to release iodine, and reacting the iodine with the benzene.

A twelfth embodiment can include the benzene sensor of any of the eighth to eleventh embodiments, wherein the iodine complex comprises an alpha-cyclodextrine-iodine complex, a β-cyclodextrine iodine complex, or any combination thereof.

A thirteenth embodiment can include the benzene sensor of any of the eighth to twelfth embodiments, wherein the iodine complex comprises a 2-hydroxypropilated-β-cyclodextrines iodine complex, a gamma-cyclodextrine iodine complex, a randomly methylated alpha-cyclodextrine-iodine complex, a randomly methylated beta-cyclodextrine-iodine complex, or any combination thereof.

A fourteenth embodiment can include the benzene sensor of any of the eighth to thirteenth embodiments, wherein the iodine complex is disposed on a substrate.

A fifteenth embodiment can include the benzene sensor of any of the eighth to fourteenth embodiments, further comprising: heating the iodine complex during the exposure of the benzene to the iodine complex.

A sixteenth embodiment can include the benzene sensor of any of the eighth to fifteenth embodiments, wherein exposing the benzene to the iodine complex comprises: allowing benzene to diffuse through an aperture into an interior of a housing, wherein the iodine complex is contained within the housing.

A seventeenth embodiment can include the benzene sensor of any of the eighth to sixteenth embodiments, wherein detecting the UV absorption intensity comprises detecting a decrease in an intensity of the reflected UV radiation.

An eighteenth embodiment can include the benzene sensor of any of the eighth to seventeenth embodiments, further comprising: determining a concentration of the benzene present.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A benzene sensor comprising:
   a substrate having an iodine complex disposed thereon;
   a radiation source configured to project UV radiation onto the complex; and
   a UV detector configured to detect a UV reflection off of the substrate having the iodine complex.

2. The benzene sensor of claim 1, further comprising:
   a housing comprising an aperture, wherein the substrate is contained within the housing, and wherein the aperture is the only opening into the housing and the substrate.

3. The benzene sensor of claim 1, further comprising:
   a heater in thermal contact with the substrate.

4. The benzene sensor of claim 1, wherein the iodine complex comprises an alpha-cyclodextrine-iodine complex.

5. The benzene sensor of claim 1, wherein the iodine complex comprises a β-cyclodextrine iodine complex.

6. The benzene sensor of claim 1, wherein the iodine complex comprises both an alpha-cyclodextrine-iodine complex and a β-cyclodextrine iodine complex.

7. The benzene sensor of claim 1, wherein the iodine complex comprises a 2-hydroxypropilated-β-cyclodextrines iodine complex, a gamma-cyclodextrine iodine complex, a randomly methylated alpha-cyclodextrine-iodine complex, a randomly methylated beta-cyclodextrine-iodine complex, or any combination thereof.

8. A method for sensing benzene comprising:
   exposing benzene to an iodine complex;
   forming an iodine-benzene complex;
   irradiating the iodine-benzene complex with UV radiation;
   detecting a UV absorption in the intensity of radiation reflected from the iodine-benzene complex; and
   determining that benzene is present based on the absorption of the UV radiation in the reflected radiation.

9. The method of claim 8, further comprising: heating the iodine complex during the exposure of the benzene to the iodine complex.

10. The method of claim 8, wherein the iodine complex comprises s cyclodextrine-iodine complex.

11. The method of claim 8, wherein forming the iodine-benzene complex comprises:
    dissociating the iodine complex to release iodine, and
    reacting the iodine with the benzene.

12. The method of claim 8, wherein the iodine complex comprises an alpha-cyclodextrine-iodine complex, a β-cyclodextrine iodine complex, or any combination thereof.

13. The method of claim 8, wherein the iodine complex comprises a 2-hydroxypropilated-β-cyclodextrines iodine complex, a gamma-cyclodextrine iodine complex, a randomly methylated alpha-cyclodextrine-iodine complex, a randomly methylated beta-cyclodextrine-iodine complex, or arty combination thereof.

14. The method of claim 8, wherein the iodine complex is disposed on a substrate.

15. The method of claim 8, further comprising: heating the iodine complex during the exposure of the benzene to the iodine complex.

16. The method of claim 8, wherein exposing the benzene to the iodine complex comprises: allowing benzene to diffuse through an aperture into an interior of a housing, wherein the iodine complex is contained within the housing.

17. The method of claim 8, wherein detecting the UV absorption intensity comprises detecting a decrease in an intensity of the reflected UV radiation.

18. The method of claim 8, further comprising: determining a concentration of the benzene present.

19. A method for sensing benzene comprising:
exposing a substrate having an iodine complex disposed thereon to a gas comprising benzene;
forming an iodine-benzene complex in response to the exposing;
irradiating the iodine-benzene complex with UV radiation from a radiation source;
reflecting at least a portion of the UV radiation from the iodine-benzene complex;
detecting a UV absorption in at least the portion of the UV radiation reflected from the iodine-benzene complex; and
determining that the benzene is present in the gas based on the detected UV absorption in the UV radiation reflected from the iodine-benzene complex.

20. The method of claim 19, further comprising: heating the substrate while exposing the substrate to the gas and irradiating the iodine-benzene complex with the UV radiation.

\* \* \* \* \*